(12) United States Patent
Ho

(10) Patent No.: US 7,765,953 B2
(45) Date of Patent: Aug. 3, 2010

(54) CARING SHELL FOR HERMIT CRAB

(76) Inventor: Chien-Hsun Ho, 8F.-2, No. 812, Fenghua Rd., Luzhu Shiang, Taoyuan County (TW)

( * ) Notice: Subject to any disclaimer, the term of this patent is extended or adjusted under 35 U.S.C. 154(b) by 136 days.

(21) Appl. No.: 12/032,055

(22) Filed: Feb. 15, 2008

(65) Prior Publication Data
US 2009/0145367 A1   Jun. 11, 2009

(30) Foreign Application Priority Data
Dec. 6, 2007   (TW) .............................. 96146515 A

(51) Int. Cl.
*A01K 61/00* (2006.01)
(52) U.S. Cl. ..................................... 119/207
(58) Field of Classification Search ............... 119/6.6, 119/207, 416, 421, 430, 452, 51.04, 174, 119/204, 208, 209, 221, 707, 850, 453, 482; 428/15, 16; 405/21, 28, 35; 43/43.14, 44.89, 43/44.96, 44.97; D30/199
See application file for complete search history.

(56) References Cited
U.S. PATENT DOCUMENTS
1,377,985 A * 5/1921 Lambert ..................... 73/273
1,874,657 A * 8/1932 Trotter ....................... 411/306
2,777,353 A * 1/1957 Willis ......................... 411/403
3,903,642 A * 9/1975 Yellin ............................ 47/69
4,250,833 A * 2/1981 Waldon ..................... 119/6.5
D281,283 S * 11/1985 Cazier ...................... D30/109
5,398,642 A * 3/1995 Harwich ................... 119/6.5
5,722,348 A * 3/1998 Phillips et al. .............. 119/452
7,256,697 B2 * 8/2007 Sakama et al. ........... 340/572.8

FOREIGN PATENT DOCUMENTS
JP       2002058380 A   *   2/2002

* cited by examiner

*Primary Examiner*—Rob Swiatek
*Assistant Examiner*—Ebony Evans
(74) *Attorney, Agent, or Firm*—Rosenberg, Klein & Lee

(57) ABSTRACT

A caring shell for hermit crab is provided. The caring shell comprises a main shell and a movable cover. The main shell has an opening, a through hole, and a receiving chamber. The receiving chamber is formed within the main shell for receiving the body of the hermit crab. The opening is formed on the front of the main shell for hermit crab moving into the receiving chamber. The through hole is formed on the main shell and communicates the receiving chamber and the outer space out of the main shell. Therefore, the body of the hermit crab within the movable cover can be obversed or touched via the through hole. The movable cover can assembled to the main shell for optionally opening and closing the through hole.

11 Claims, 5 Drawing Sheets

CARING SHELL FOR HERMIT CRAB

BACKGROUND OF THE INVENTION

1. Field of the Invention

The present invention is related to a caring shell, and more particular to a caring shell for hermit crab.

2. Description of Related Art

The hermit crab usually lives in a natural spiral shell as a "moving house" to protect its weak body. Recently, people pick up seashell and spiral shell as decorations. However, it is a pity for a hermit crab that the hermit crab may live in a bottle cap whenever the hermit crab can not find a spiral shell as its house.

There are over eight hundred categories of hermit crabs. Some of them are very popular pets; especially, land hermit crabs. There are about ten categories of land hermit crabs in the world. Generally speaking, the land crabs can live thirteen years under proper living environment.

Therefore, the artificial spiral shell for hermit crab is provided as a product. Please refer to the Japan patents, such as JP9-275850 and JP2002-58380, which are the techniques relative to the artificial spiral shell for hermit crabs. However, the characteristic of the patents are just relative to the appearances of the artificial spiral shells. For example, an artificial spiral shell for hermit crab as disclosed in Japanese patent JP9-275850 looks like Santa Claus. It is interesting that the hermit crab carries the shell on the back, and goes around everywhere just like Santa Claus going around everywhere.

Basing on the problems as mentioned, for the purpose of providing proper living environment and well physiological care for the hermit crab, it is necessary to provide a caring shell for the hermit crab living therein, so that the living condition will be more suitable and comfortable for the hermit crab.

SUMMARY OF THE INVENTION

Accordingly, the objective of the present invention provides a caring shell for hermit crab. The hermit crab can be bred, treated, cared, and observed, and it is convenient for any one else to observe the hermit crab via the caring shell. The caring shell is also provided as a safe living place and a well ecological environment for hermit crab. Moreover, for stimulating the motivation of the owner to breed and take care of the hermit crabs, the caring shell can be provided as a peripheral funny device, or be provided with charming appearance, such as transparent or colorful painted appearance, which catches the owner's eyes.

The present invention provides a caring shell for hermit crab. The caring shell further comprises a main shell and a movable cover.

The main shell has an opening, a through hole, and a receiving chamber. The main shell is made of glasses, plastic, or ceramics. The outer surface of the main shell is capable of being coated with colorful paint or transparent material, so that it is capable of observing the hermit crab living inside of the main shell.

The receiving chamber is formed within the main shell for receiving the body of the hermit crab. The opening is formed on the front of the main shell for hermit crab moving into the receiving chamber and an outer space out of the main shell. The through hole is formed on the main shell and communicates the receiving chamber and the outer space.

In the preferred embodiments of the present invention, the movable cover can be provided in many forms as disclosed below. Nevertheless, the movable cover is movably assembled to the main shell for optionally opening and closing the through hole.

The present invention not only can provide a safe living place and a well ecological environment for hermit crab, but also allow an owner to breed, treat, cared, and observe the hermit crab through the design of the through hole and the movable cover. It also can stimulate the motivation of the owner to breed and take care of the hermit crabs via effective means of that the caring shell can be provided as a peripheral funny device, or be provided with charming appearance, such as transparent or colorful painted appearance, which catches the owner's eyes.

The objective of the present invention will no doubt become obvious to those of ordinary skill in the art after reading the following detailed description of the preferred embodiment, which is illustrated in the various figures and drawings.

BRIEF DESCRIPTION OF THE DRAWINGS

The present invention can be fully understood from the following detailed description and preferred embodiment with reference to the accompanying drawings, in which.

DETAILED DESCRIPTION OF THE PREFERRED EMBODIMENTS

Figure 1:
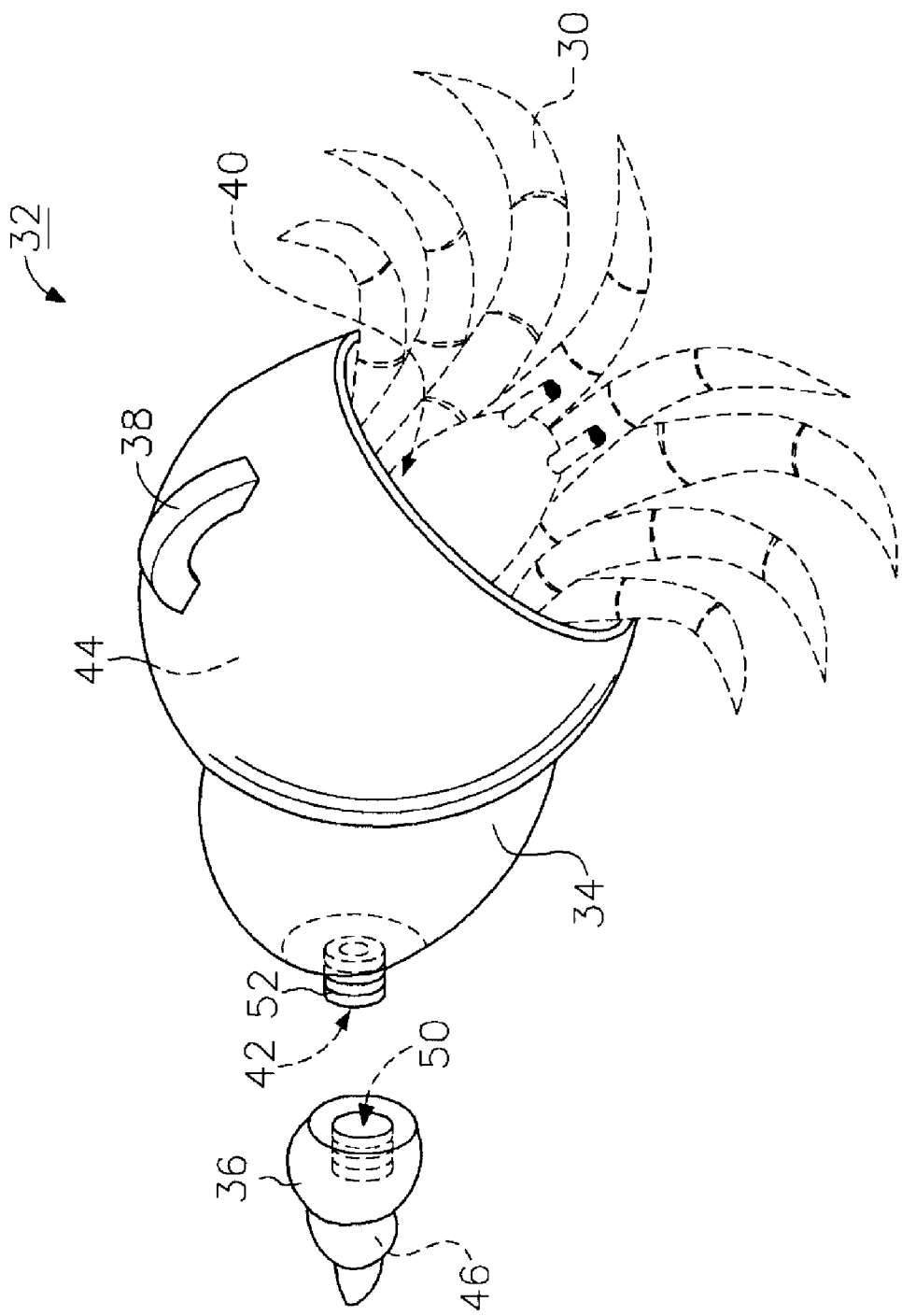
FIG. 1 is a schematic diagram of the first embodiment of the caring shell according to the present invention.

Please refer to FIG. 1 which illustrates the schematic diagram according to the first embodiment of the present invention. The present invention provides a caring shell 32 for hermit crab 30. The caring shell 32 further comprises a main shell 34 and a movable cover 36.

The main shell 34 has an opening 40, a through hole 42, and a receiving chamber 44. The main shell 34 defines an outer space out of the main shell 34. The main shell 34 is made of glasses, plastic, or ceramics. The outer surface of the main shell 34 is capable of being coated with paint, or transparent material for observing the hermit crab 30 inside of the main shell 34.

The receiving chamber 44 is formed within the main shell 34 for receiving the body of the hermit crab 30. The opening 40 is formed on the main shell 34. The preferred position of the opening 40 is deposed on the front of the main shell 34, as shown on FIG. 1. The opening 40 communicates the receiving chamber 44 and the outer space of the main shell 34 for the hermit crab 30 moving into the receiving chamber 44 and the outer space.

The through hole 42 is formed on the main shell 34 and communicates the receiving chamber 44 and the outer space out of the main shell 34. The position of the through hole 42 depends on different needs. The main shell 34 further has a fixture 38 for binding a cord on the outer surface thereof for a pet owner pulling or limiting the action of the hermit crab 30 via the cord.

The movable cover 36 is movably assembled to the main shell 34 for optionally opening and closing the through hole 42. The movable cover 36 prevents the water within the main shell 34 escaping therethrough.

The whole caring shell 32 can be formed as a spiral shell. The opening 40 is deposed on the front of the spiral shell. The through hole 42 is deposed on the rear of the spiral shell. The movable cover 36 can be formed as a tail of the spiral shell. When the movable cover 36 is covered on the through hole 42, as shown on the figures, the moveable cover 36 and the through hole 42 are assembled as a whole spiral shell. The shape of the movable cover 36 is not limited as the spiral shell. The shape of the movable cover 36 can be any designable shape, such as a ball, a cone, and so on. The different embodiments and assembling types of the movable cover 36 and the caring shell 32 are described below.

In the first embodiment, the movable cover 36 further has a bolt hole 50 and/or a receiving space 46 within the movable cover 36. The bolt hole 50 can communicate with the receiving space 46. The main shell 34 further comprises a connection bolt 52 being fit for the bolt hole 50 having the through hole 42. The connection bolt 52 is assembled to the bolt hole 50 to make the movable cover 36 be assembled to the main shell 34. In this embodiment, the bolt hole 50 can be a threaded hole, and the connection bolt can be a screw, as shown on FIG. 1. The screw is assembled to the threaded hole to make the movable cover 36 be assembled to the main shell 34.

Figure 2:
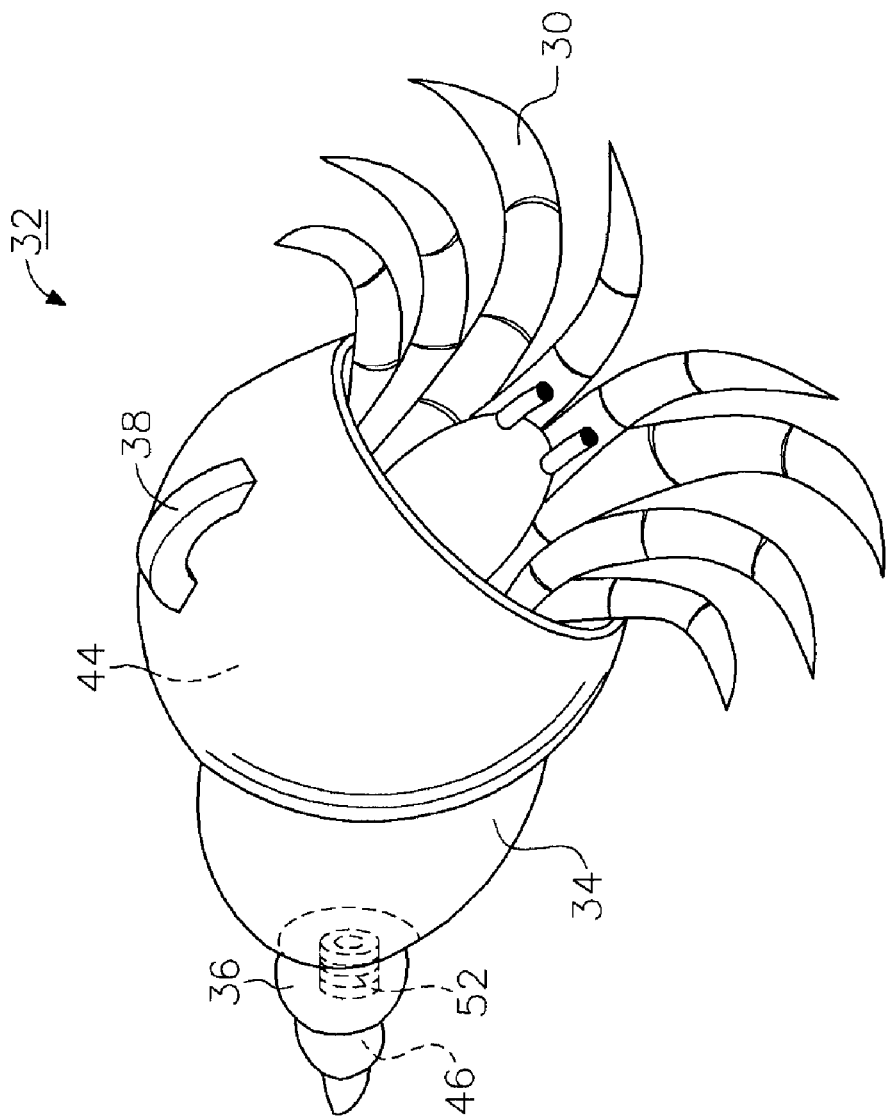
FIG. 2 is an assembled view according to the present invention.

Please refer to FIG. 2, illustrating the movable cover 36 and the main shell 34 assembled. The movable cover 36 is like the tail of the spiral shell, and the movable cover 36 and the main shell 34 are like a beautiful and natural spiral shell. A wet sponge can be put into the receiving space 46 to keep the water that the hermit crab 30 needs. Nutrition, such as calcium, can be put into the receiving space 46 for the hermit crab 30.

Figure 3:
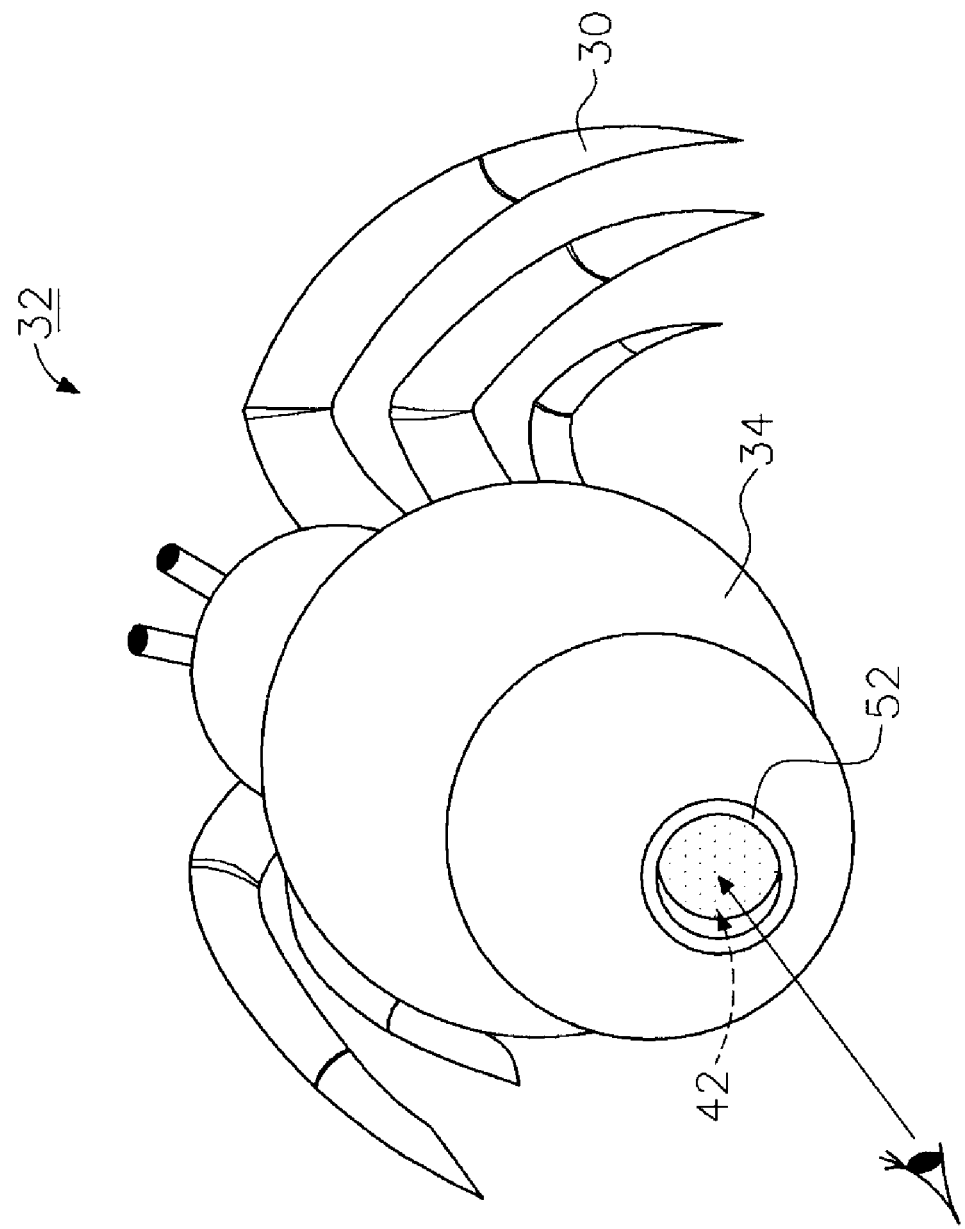
FIG. 3 is a rear view of the first embodiment according to the present invention.

Please refer to FIG.3, illustrating the rear view of the first embodiment. A pet owner can observe the hermit crab 30 within the main shell 34 via the through hole 42, impregnate seeds to the female hermit crab 30 via the through hole 42, and put nutrition into the receiving chamber, and the hermit crab 30 can absorb from skin. Moreover, a pet owner can use a cotton swab to push the hermit crab 30 to make it leave the main shell 34 and force the hermit crab 30 changing shell. A pet owner can anesthetize or perform a surgical operation for the hermit crab 30 for medical purpose, also.

Figure 4:
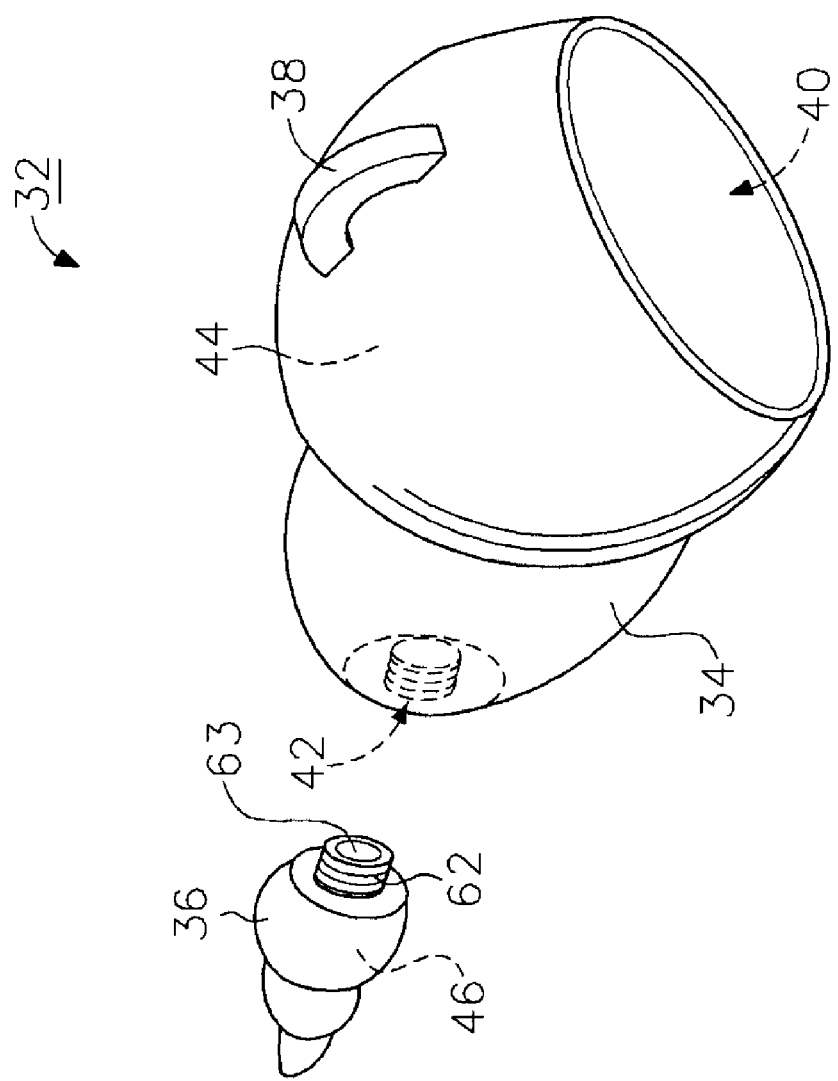
FIG. 4 is a schematic diagram of the second embodiment of the caring shell according to the present invention.

Please refer to FIG. 4, illustrating a schematic diagram of the second embodiment of the present invention. The movable cover 36 further comprises a connection bolt 62 being fit for the through hole 42. The connection bolt 62 has an aperture 63 communicating with a receiving space 46 within the movable cover 36. The movable cover 36 is assembled to the main shell 34 when the connection bolt 62 is assembled to the through hole 42. In this embodiment, the connection bolt can be a screw, and the through hole can be a threaded hole. The screw is assembled to the threaded hole to make the movable cover 36 be assembled to the main shell 34.

Figure 5:
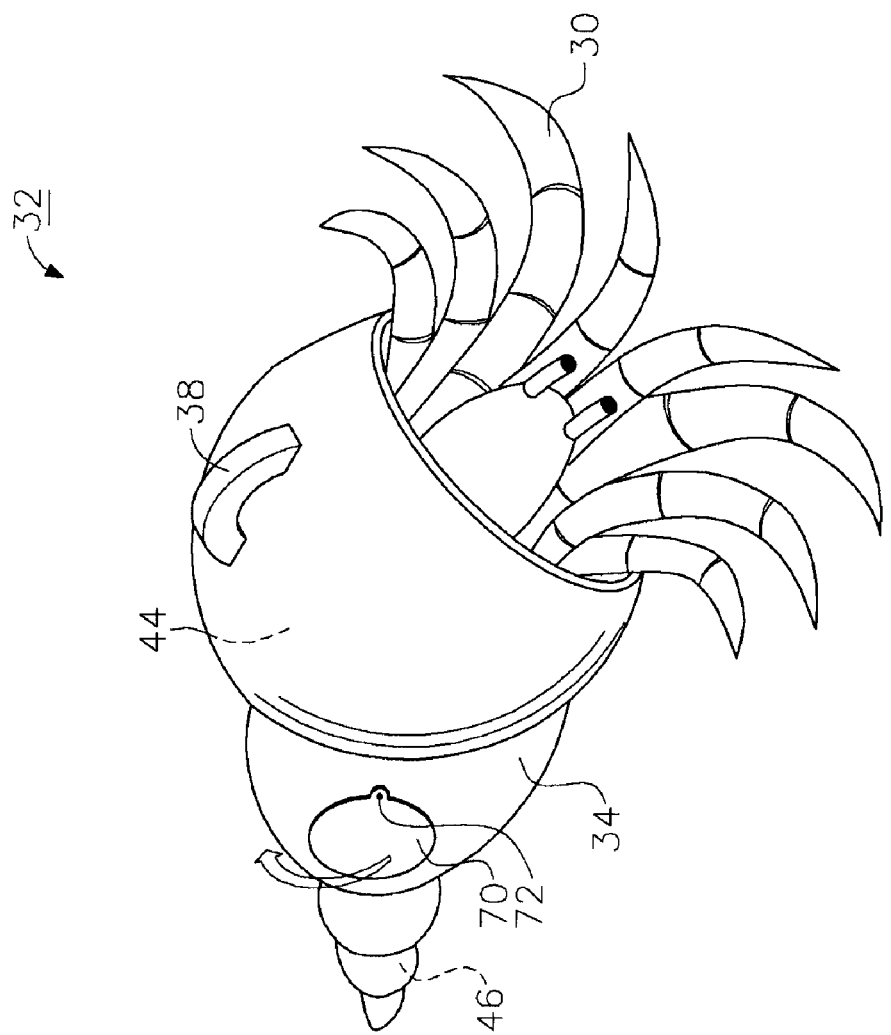
FIG. 5 is a schematic diagram of the third embodiment of the caring shell according to the present invention.

Please refer to FIG. 5, the schematic diagram of the third embodiment of the present invention. The movable cover 70 can be a plate shape. The movable cover 70 is pivotally connected on the main shell 34 via a connecting shaft 72. In general, the movable cover 70 covers the through hole 42 to prevent the hermit crab 30 from losing water. The movable cover 70 uncovers the through hole 42 for some reasons, such as observing or taking care to the hermit crab 30. Although the third embodiment is not as beautiful as the others and the functions of the third embodiment is lesser than others, the third embodiment is cheaper than others.

The present invention not only can provide a safe living place and a well ecological environment for hermit crab 30, but also allow an owner to breed, treat, care for, and observe the hermit crab 30 through the design of the through hole 42 and the movable cover 36, 70. It also can stimulate the motivation of the owner to breed and take care of the hermit crab 30 via effective means of that the caring shell 32 which can be provided as a peripheral funny device, or be provided with charming appearance, such as transparent or colorful painted appearance, which catches the owner's eyes.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A caring shell for surrogate use upon a hermit crab, comprising:
    a main shell configured to be transportably worn by a hermit crab, defining generally a seashell shaped body, and having a receiving chamber forming within the seashell shaped body; the seashell shaped body having an opening formed at a front lateral side thereof, the receiving chamber communicating with the outer space for the hermit crab to move between the receiving chamber and the outer space; the seashell shaped body having a through hole formed at a rear lateral side thereof communicating with the receiving chamber; and
    a movable cover movably assembled to the rear side of the seashell shaped body of the main shell for optionally opening and closing the through hole, wherein the movable cover further has a bolt hole communicating to a receiving space within the movable cover, the main shell further comprises a connection bolt being fit for the bolt hole and the connection bolt having the through hole, and the connection bolt is assembled to the bolt hole to make the movable cover be assembled to the main shell.

2. The caring shell as claimed in claim 1, wherein the connection bolt is a screw, the bolt hole is a threaded hole, and the screw is assembled to the threaded hole to make the movable cover be assembled to the main shell.

3. The caring shell as claimed in claim 1, wherein the movable cover further comprises a connection bolt being fit for the through hole and the connection bolt having an aperture communicating with a receiving space within the movable cover, and the movable cover is assembled to the main shell when the connection bolt is assembled to the through hole.

4. The caring shell as claimed in claim 3, wherein the connection bolt is a screw, the through hole is a threaded hole, and the screw is assembled to the threaded hole to make the movable cover be assembled to the main shell.

5. The caring shell as claimed in claim 1, wherein the movable cover is pivotally connected to the main shell.

6. The caring shell as claimed in claim 1, wherein the main shell has a fixture for binding a cord.

7. The caring shell as claimed in claim 1, wherein the main shell is made of glasses, plastic, or ceramics.

8. The caring shell as claimed in claim 1, wherein the main shell is made of a transparent material.

9. The caring shell as claimed in claim 1, wherein the main shell is capable of being coated with paint.

10. The caring shell as claimed in claim 1, wherein the main shell is formed generally with a spiral seashell shape.

11. The caring shell as claimed in claim 10, wherein the movable cover is formed generally with a spiral tail shape for the main shell.

* * * * *